(12) United States Patent
Kumar et al.

(10) Patent No.: US 6,397,682 B2
(45) Date of Patent: Jun. 4, 2002

(54) INTERGRANULAR DEGRADATION ASSESSMENT VIA RANDOM GRAIN BOUNDARY NETWORK ANALYSIS

(75) Inventors: Mukul Kumar, San Ramon; Adam J. Schwartz, Pleasanton; Wayne E. King, San Ramon, all of CA (US)

(73) Assignee: The United States of America as represented by the Department of Energy, Washington, DC (US)

( * ) Notice: Subject to any disclaimer, the term of this patent is extended or adjusted under 35 U.S.C. 154(b) by 0 days.

(21) Appl. No.: 09/780,089

(22) Filed: Feb. 9, 2001

Related U.S. Application Data

(60) Provisional application No. 60/181,453, filed on Feb. 10, 2000.

(51) Int. Cl.[7] .................................................. G01B 5/30
(52) U.S. Cl. ........................................... 73/760; 73/800
(58) Field of Search .......................... 73/760, 773, 781, 73/788, 800; 148/559, 668

(56) References Cited

U.S. PATENT DOCUMENTS

| | | | | |
|---|---|---|---|---|
| 4,489,425 A | * | 12/1984 | Borgonovi | 378/72 |
| 4,686,631 A | * | 8/1987 | Ruud | 378/72 |
| 4,810,447 A | * | 3/1989 | Csillag | 264/125 |
| 4,832,708 A | * | 5/1989 | Csillag | 264/122 |
| 5,651,839 A | | 7/1997 | Rauf | 148/95 |
| 5,702,543 A | | 12/1997 | Palumbo | 148/592 |
| 5,817,193 A | | 10/1998 | Palumbo | 148/325 |
| 5,993,893 A | * | 11/1999 | Kikuchi | 427/255.18 |
| 6,086,691 A | | 7/2000 | Lehockey et al. | 148/706 |
| 6,129,795 A | | 10/2000 | Lehockey et al. | 148/608 |

OTHER PUBLICATIONS

Warrington and Boon, "Ordered Structures in Random Grain Boundaries: Some Geometrical Probabilities", Acta Metallurgica, vol. 23, May 1975, pp. 599–607, Pergamon Press, New York, USA.

Grimmer, Bollmann and Warrington, "Coincidence–Site Lattices and Complete Pattern–Shift Lattices in Cubic Crystals", Acta Crystallographica, A30, 1974, pp. 197–207, International Union of Crystallography, Copenhagen, Denmark.

Tadao Watanabe, "An Approach to Grain Boundary Design for Strong and Ductile Polycrystals", Res Mechanica 11 (1984) pp. 47–84, Elsevier Applied Science Publishers, London, UK.

Palumbo and Aust, "Structure–Dependence of Intergranular Corrosion in High Purity Nickel", Acta Metallurgica et Materialia, vol. 38, 11, 1990, pp. 2343–2351, Permon Press, United Kingdom.

Wells, Stewart, Herber, Scott and Williams, "The Use of Percolation Theory to Predict the Probability of Failure of Sensitized, Austenitic Stainless Steels by Intergranular Stress Corrosion Cracking", journal Corrosion, vol. 45, No. 8, Aug. 1989, pp. 649–660, National Association of Corrosion Engineers, Texas, USA.

Randle and Brown, "Development of grain misorientation texture in terms of coincident site lattice structures, as a function of thermomechanical treatments", Philosophical Magazine A, vol. 59, No. 5, 1989, pp. 1075–1089, Taylor and Francis Ltd., London UK.

(List continued on next page.)

Primary Examiner—Max Noori
(74) Attorney, Agent, or Firm—Randall W. Chang; William C. Daubenspeck; Virginia B. Caress

(57) ABSTRACT

A method is disclosed for determining the resistance of polycrystalline materials to intergranular degradation or failure (IGDF), by analyzing the random grain boundary network connectivity (RGBNC) microstructure. Analysis of the disruption of the RGBNC microstructure may be assess the effectiveness of materials processing in increasing IGDF resistance. Comparison of the RGBNC microstructures of materials exposed to extreme operating conditions to unexposed materials may be used to diagnose and predict possible onset of material failure due to

4 Claims, 2 Drawing Sheets

OTHER PUBLICATIONS

Palumbo, Aust, Erb, King, Brennenstuhl and Lichtenberger, "On Annealing Twins and CSL Distributions in F.C.C. Polycrystals", Phys Stat. Sol. (a) 131, 1992, pp. 425–428, Akademie Verlag GmbH, Berlin Germany Miyazawa, Iwasaki, Ito and Ishida, "Combination Rule of S Values at Triple Junctions in Cubic Polycrystals", Acta Crystallographica, A52, 1996, pp. 787–796, Internation Union of Crystallography, United Kingdom.

D.G. Brandon, "The Structure of High–Angle Grain Boundaries". Acta Metallurgica, vol. 14, Nov. 1966, pp. 1479–1484, Pergamon Press, New York, USA, United Kingdom.

Y. Pan, B. Adams, T. Olson, N. Panayotou, "Grain–Boundary Structure Effects on Intergranular Stress Corrosion Cracking of Alloy X–750", Acta Materialia, vol. 44, No. 12, (1996) pp. 4685–4695, Elsevier Publishers, Oxford, UK.

H. Grimmer, "A method of determining the coincidence site lattices for cubic crystals", Acta Crystallographica Section A–Foundations of Crystallography, A30, (1974) pp. 680, Internation Union of Crystallography, Copenhagen, Denmark.

Presentation by the inventors describing aspects of the invention, presentation entitled "The Role of Twinning in the Optimization of The Grain Boundary Character Distribution", UCRL–JC–131664, dated Jan. 8, 1999, presented Mar. 1, 1999 at Int'l Symposium on Advances in Twinning, TMS–AIME Annual Meeting, San Diego, CA.

Presentation by the inventors describing aspects of the invention, presentation entitled "Modifications in the Grain Boundary Character Distribution in FCC Materials Through Thermomechanical Processing", ICRL–JC–133852, dated Mar. 1999, for submittal to International Conference on Texture of Materials, Montreal, Canada, Aug. 9–13, 1999.

Presentation by the inventors describing aspects of the invention, presentation entitled "Influence of Processing Method on The Grain Boundary Character Distribution and Network Connectivity", UCRL–JC–134727, MRS Proceedings, vol. 586. 1999, Boston, MA.

Journal article by the inventors describing aspects of the invention, article entitled "Modifications inthe Microstructural Topology in FCC Materials Through Thermomechanical Processing", UCRL–JC–135761, published in journal Acta Materialia, vol. 48, Issue 9, May 29, 2000, United Kingdom.

Presentation by the inventors describing aspects of the invention, presentation entitled "Experimental Studies in Microstructural Engineering", UCRL–VG–135303, Aug. 23, 1999, presented at Multiple Length Scale Simulation of Materials Microstructure and Evolution Theory Institute at Argonne National Laboratory, Chicao, IL.

Presentation by the inventors describing aspects of the invention, presentation entitled "Effect of Sequential Thermomechanical Processing on the Connectivity of the Random Grain Boundary Network", UCRL–VG–137348, presented at Electric Power Research Institute (EPRI) 2000 Workshop on PWSCC of Alloy 600 in PWRs, Feb. 14–16, 2000, St. Pete Beach, Florida.

Grant proposal by the inventors describing aspects of the invention, proposal entitled "Random Grain Boundary Network Connectivity as a Predictive Tool", UCRL–Prop–137349, Feb. 2000, Nuclear Energy Research Initiative Proposal.

* cited by examiner

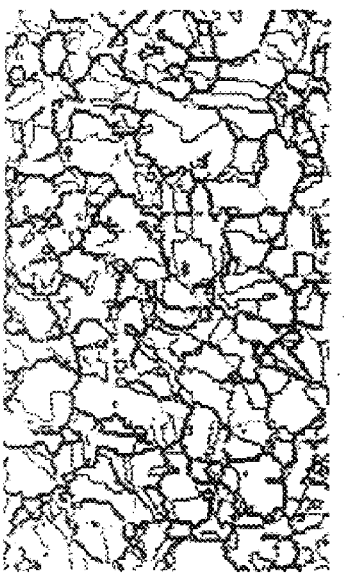
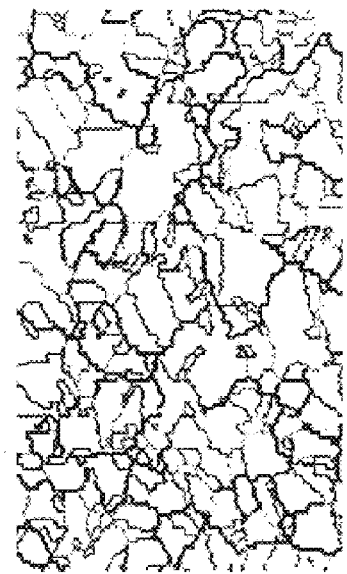
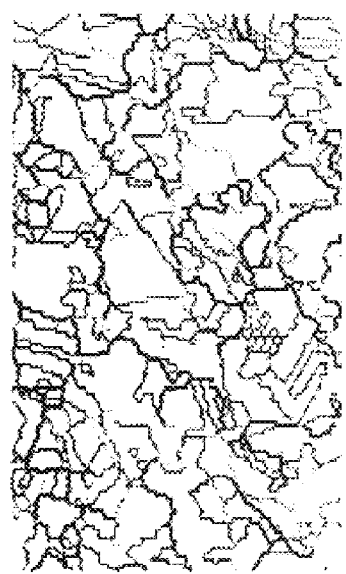
FIG. 2A         FIG. 2B         FIG. 2C
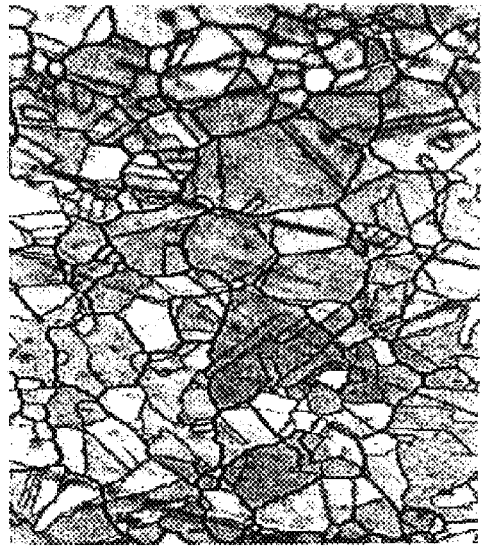
FIG. 3A             FIG. 3B

INTERGRANULAR DEGRADATION ASSESSMENT VIA RANDOM GRAIN BOUNDARY NETWORK ANALYSIS

CROSS-REFERENCE TO RELATED APPLICATIONS

This application claims the benefit of U.S. Provisional Application No. 60/181,453, filed Feb. 10, 2000.

STATEMENT OF GOVERNMENT INTEREST

The United States Government has rights in this invention pursuant to Contract No. W-7405-ENG-48 between the U.S. Department of Energy and the University of California.

BACKGROUND OF THE INVENTION

The present invention relates generally to resistance of polycrystalline materials to intergranular degradation or failure (IGDF), and particularly to disruption of the material's random grain boundary network connectivity (RGBNC) structure as an indicator of the material's resistance to IGDF. This indicator may be used to assess the effectiveness of engineering processes to increase the material's IGDF resistance or as a diagnostic tool to detect possible onset of material failure due to IGDF.

DESCRIPTION OF RELATED ART

The phenomenon of stress corrosion cracking (SCC) in structural materials due to the collective actions of stress, material microstructure, and environment have been recognized for many years, and the mechanisms have been extensively investigated. The SCC process is believed to be governed by the subprocesses of crack initiation and crack propagation. The method of grain boundary engineering is currently seen as one means of modifying materials in order to increasing the SCC resistance of the grain boundaries.

A grain boundary is formed where two single-crystal grains in a polycrystalline aggregate meet. The boundary is characterized by its macroscopic and microscopic degrees of freedom. In its ideal form, the boundary is planar and defined by the misorientation of the grains on either side of the boundary (two degrees of freedom for the axis of misorientation and one for the misorientation angle) and the plane of the interface (two degrees of freedom). The rigid-body shifts, parallel and perpendicular to the boundary plane, comprise the three microscopic degrees of freedom. The general grain boundary is not planar and can take on curvatures consistent with the energetics of the system.

It is common practice to describe grain boundaries by the misorientation of one grain with respect to another. It is convenient to use the axis-angle notation to denote rotation axis and the rotation angle necessary to transform one into the other. Consider two crystal lattices misoriented with respect to each other and allowed to interpenetrate. At certain axis-angle pairs, the lattices form special patterns characterized by the coincident site lattice (CSL) notation (described by H. Grinrner, *Acta Crystallographica Section A—Foundations of Crystallography*, A30 (1974)680). In this notation, the misorientation is denoted as $\Sigma n$ where n is the reciprocal density of coincident lattice sites, n is always odd. The CSL notation is geometrical only and Ad disregards the plane of the grain boundary and the microscopic degrees of freedom. Although one would not expect macroscopic properties to correlate with $\Sigma n$, however there is strong evidence that such a correlation exists for some properties.

Grain boundaries are often grouped into broad classes, such as low- and high-angle, twist and tilt, and special and random. The first class is based on structure and energy criteria while the second and third classes are strictly geometrical in nature. Conventionally, the delimiting angle separating low- from high-angle boundaries is 15 degrees for cubic crystals. This is approximately the angle where it is no longer possible to discern well-separated dislocations forming the boundary.

Strictly speaking, special boundaries (boundaries that have low $\Sigma$ and exhibit special properties) occur at well-defined misorientations, but it has been shown that boundaries near an exact $\Sigma$ misorientation can exhibit $\Sigma$-like properties. The acceptance angle, $\Delta\phi$, over which boundaries exhibit $\Sigma$-like properties is usually expressed as:

$$\Delta\phi = \Delta\phi_0 \Sigma^{-m}$$

where the prefactor $\Delta\phi_0$ is 15 degrees, and m=1/2 according to the Brandon criterion [D. G. Brandon, Acta Metallurgica, 14 (1966) 1479].

Not all boundaries that meet this criterion exhibit special properties. Generally speaking, special boundaries are those boundaries with $\Sigma \leq 29$. Other boundaries, including $\Sigma > 29$ are considered random. This arbitrary cut-off value of $\Sigma 29$ for cubic crystalline materials, was first suggested by Watanabe [Watanabe, T., J. Physique, 1985, 46(C4), 555]. The distribution of boundary types with respect to $\Sigma$ is called the grain boundary character distribution (GBCD).

Many important physical and mechanical properties of materials are intimately coupled to microstructural features such as chemistry, grain size and shape, texture, and the presence of second phases and precipitates. It is possible to tailor the microstructure of metals alloys through thermomechanical processing to obtain orders of magnitude improvement in resistance to corrosion, stress corrosion cracking, creep and possibly to irradiation assisted stress corrosion cracking. These processing methods have generically become known as grain boundary engineering.

In grain boundary engineering, properties such as those described above have been found empirically to correlate with the fraction of "special" boundaries in the microstructure. Palumbo (G. Palunbo, U.S. Pat. Nos. 5,817,193 and 5,702,543) has in described methods by which a material can be processed to increase the fraction of special grain boundaries in a microstructure. This typically involved sequential thermomechanical processing (TMP) where a material is deformed by a moderate amount, e.g. 20% and annealed at a relatively high temperature for a relative short time. The process of deformation and annealing is repeated until the desired special fraction is obtained.

In a few documented cases, intergranular stress corrosion cracking (IGSCC) has been observed to propagate along the interconnected random grain boundary network. Adams et al [Y. Pan, B. L. Adams, T. Olson, and N. Panayotou, *Acta Materialia* 44 (1996)4685] have analyzed crack path dependence of IGSCC of alloy X-750. The study examined some 818 cracked triple junctions. The choice of which boundary the crack advances upon was studied as a function of misorientation and inclination relative to the stress axis. The general observation is that random boundaries are most susceptible to cracking when the direction of forward propagation of the crack lies within an angular range of ~20 degrees about the crack plane. Low angle ($\Sigma 1$) and $\Sigma 3$ boundaries are observed not to crack for any plane inclination. Some CSL boundaries lying in the range $\Sigma 5-\Sigma 49$ did crack; however, when the plane inclination was considered, boundaries whose planes lie sufficient close to the coherence plane(s) were observed not to crack. Watanabe [Watanabe, Res Mechanica, 1984, 11, pp 47–84] states that low-angle and coincidence high-angle boundaries are resistant to segregation-assisted IG fracture, whereas random high-angle boundaries are preferential sites for IG fracture in most situations.

It has been found that properties that are favorably influenced by grain boundary engineering tend to have percolative mechanisms, which depend on the topology of the grain boundary network. Wells et al. [Wells, D. B., Stewart, J., Herbert, A. W., Scott, P. M. and Williams, D. E., Corrosion, 1989, 45, 649], on the basis of a bond percolation formulation, suggested an appropriate statistical function that would describe when the assembly of grain boundaries in the microstructure attained a critical value of active segments. On the basis of these simulations, Wells predicted that the minimum fraction of random boundaries in a three-dimensional lattice structure that would lead to the formation of a one-dimensional continuous linear chain was 0.23. However, when a planar section, based on an approximation of the two-dimensional microstructure to a honeycomb network, was considered then this boundary fraction reached a value of approximately 0.65. This suggests that the probability of cracks propagating through the microstructure would be considerably reduced as the special fraction increases beyond 0.35.

Advances in the engineering of grain boundaries in materials have been facilitated in recent years by a scanning electron microscope (SEM) technique, known as electron backscattered diffraction (EBSD), for automated indexing of electron backscattered diffraction Kikuchi patterns. This technique has largely superceded other experimental techniques, such as transmission electron microscopy (TEM) and electron channeling in the SEM, for the determination of the GBCD due to the relatively straightforward specimen preparation and the large number of orientation measurements attainable in a relatively short period of time. Thus, advances in the engineering of grain boundaries can be ascribed due to the following factors: (1) recognition that grain boundaries play an important role in a number of materials properties, (2) recent evidence that TMP can alter the GBCD, and (3) ease of characterization of the GBCD by the automated EBSD patterns technique.

The SEM-based set-up automatically acquires and processes EBSD patterns for determination of local orientations, misorientations, and microtexture. It allows the orientation at spatially specific points in planar sections of the microstructure to be measured and directly correlated with results from other imaging techniques such as optical or scanning electron microscopy. The acquisition of an EBSD pattern requires a highly collimated, stationary electron probe focused on a steeply inclined specimen. The interaction of the electron beam and the specimen generates an EBSD pattern by the backscattering of electrons from favorably oriented crystal planes. Individual orientation measurements are made at discrete points on a sample; the locations of the points are defined by a grid of dimensions prescribed by the user (both in the width and height of the grid as well as the spacing between points on the grid). At each point in the grid, the backscattered Kikuchi diffraction pattern is captured, frame averaged and automatically indexed. The three Euler angles that describe the orientation are recorded along with coordinates describing the position. Thus, images (or maps) can be generated by mapping the crystal orientation onto a color or grayscale and shading each point on the grid according to some aspect of the crystal orientation. Alternatively, misorientations between points can be indicated by drawing boundaries that are color coded by type of boundary, as for example, special or random.

SUMMARY OF THE INVENTION

An object of the present invention is a method for determining the resistance of polycrystalline materials to intergranular degradation or failure (IGDF), by analysis of the random grain boundary network connectivity (RGBNC).

Another object of the present invention is a method for confirming the improvement in IGDF resistance of polycrystalline materials that have been subjected to materials processing.

Another object of the present invention is a method for inspecting existing polycrystalline material structures operating under extreme conditions (such as high temperature, high stress or corrosive environments), to detect susceptibility to potential intergranular degradation and/or failure. The method comprising comparing stereological parameters from the RGBNC for the existing stressed material to the analogous parameters from the pre-existing unstressed material's RGBNC.

As discussed earlier, conventional grain boundary engineering efforts currently focus on increasing the ratio of "special" to "random" grain boundaries. However, the inventors conclude that merely increasing the ratio, although necessary is not sufficient to improve properties such as resistance to intergranular degradation or failure. In fact, IG degradation and failure, which include IG corrosion and IG fracture, are primarily dependent on the spatial distribution and interconnectivity of the boundaries prone to crack propagation, i.e. the grain boundary network. In particular, the degree to which the random grain boundary network connectivity (RGBNC) has been disrupted by the special boundaries may be used as a key indicator of a material's IGDF resistance. Assessment of the RGBNC after a material has undergone processing, such as thermomechanical working, can indicate whether the material's IGDF resistance has improved. Alternatively, comparison of the RGBNC for a material in service under extreme operating conditions (high temperature, high stress, highly corrosive environment, or combinations of the foregoing) against the RGBNC for the same material unexposed to the extreme conditions can provide an indicator whether the service material might undergo failure due to an IGDF mechanism.

BRIEF DESCRIPTION OF THE DRAWINGS

FIGS. 2A–2C illustrate RGBNC maps for multiple sequentially strain-recrystallized Inconel 600 annealed at 1000 degrees C. in the following conditions: (a) as-received condition; (b) after three processing cycles; and (c) after four processing cycles.

FIGS. 3A, 3B illustrate RGBNC maps for ofe Cu annealed at: a) 560 degrees C.; b) 800 degrees C.

DETAILED DESCRIPTION OF THE INVENTION

Abbreviations

Figure 1:
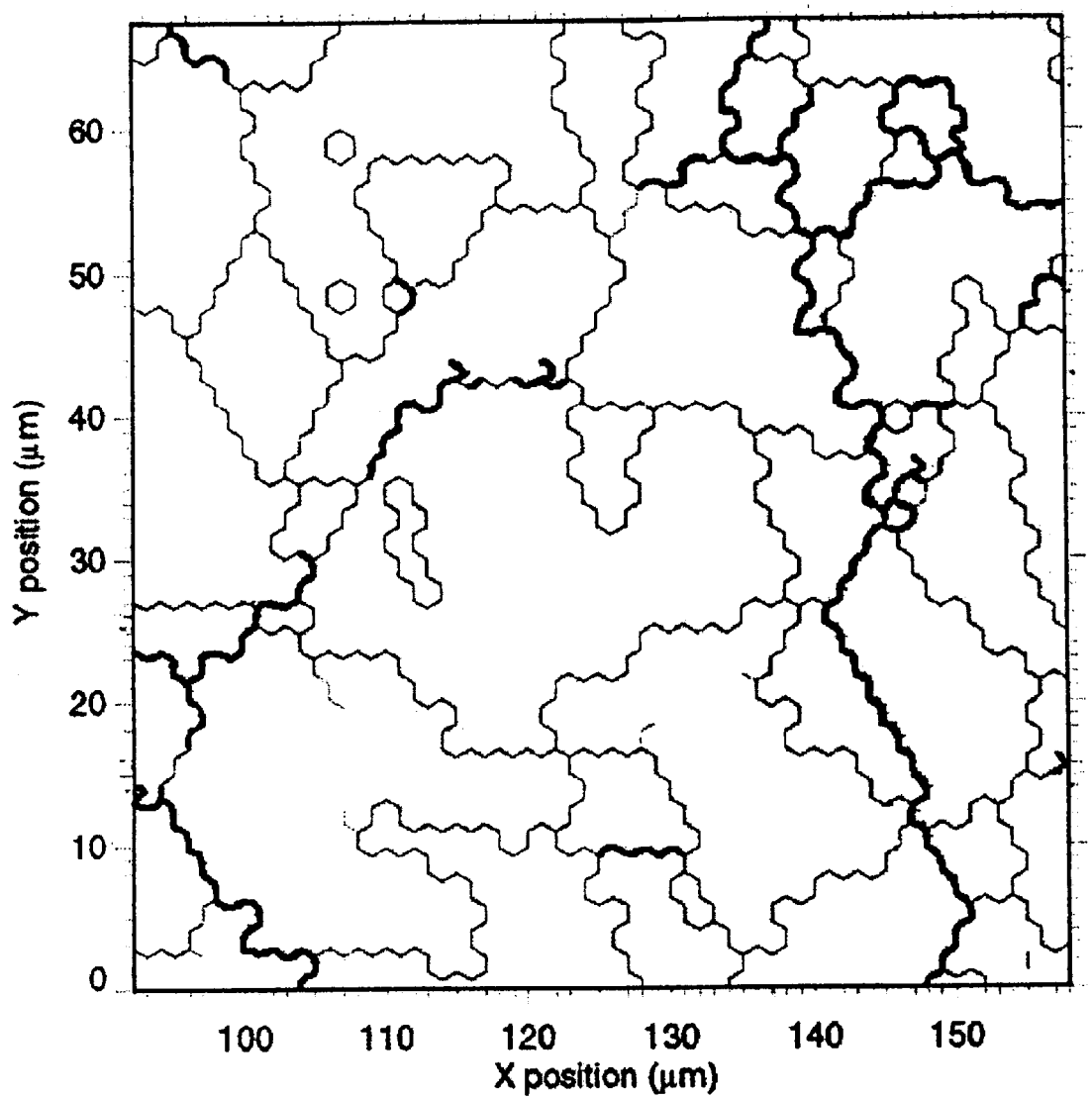
FIG. 1 illustrates a simplified sample RGBNC map for Inconel 600 based on identified random boundary segments in an EBSD dataset.

| | |
|---|---|
| $\Sigma n$ | notation from the CSL model denoting a grain boundary wherein n is the reciprocal of the ratio of the number of coincident lattice sites to the total for the two grains |
| CSL | Coincident Site Lattice |
| EBSD | electron back scattered diffraction |
| GBCD | grain boundary character distribution - the microstructural property that describes the proportions of "special" and "random" grain boundaries with respect to the "Coincident Site Lattice" model. |
| IG | intergranular |
| IGDF | intergranular degradation or failure |
| IGSCC | intergranular stress corrosion cracking |

-continued

| | |
|---|---|
| ofe Cu | oxygen free electronic copper |
| OIM™ | orientation imaging microscopy - commercial version of EBSD, trademarked by TSL, Inc. |
| RB | random boundary |
| RGBNC | random grain boundary network connectivity |
| SB | special boundary |
| SCC | stress corrosion cracking |
| SEM | scanning electron microscopy |
| SR | strain-recrystallization processing: the application of moderate levels of deformations (between 20 and 30%) followed by intermediate to high temperature (0.5–0.8$T_m$) anneals. |
| TG | transgranular |
| $T_m$ | absolute melting temperature |
| TMP | thermomechanical processing |
| O-CSL | triple junction (point) having three random boundaries |
| 1-CSL | triple junction (point) having one special boundary and two random boundaries |
| 2-CSL | triple junction (point) having two special boundaries and one random boundary |
| 3-CSL | triple junction (point) having three special boundaries |
| Definitions | |
| high angle boundary | misorientation angle is lower than 15 degrees |
| low angle boundary | misorientation angle is greater than or equal to 15 degrees |
| random boundary | boundary having Σ value greater than a predetermined valued, said value being 29 for cubic crystalline materials |
| special boundary | boundary having Σ value less than or equal to a predetermined valued, said value being 29 for cubic crystalline materials |
| special fraction | ratio of special boundaries to random boundaries |
| triple junction | point at which three boundaries intersect |

The probabilistic nature of the approach proposed by Wells described earlier, does not fully incorporate the possible correlations that exist in a grain boundary network. This suggests that the methodology for optimization of the microstructural topology cannot solely be based on improvements in the GBCD, though that is a necessary parameter. Moreover, the path length that was assumed in the probabilistic analyses may be an overestimation of the critical length in the materials phenomenon in consideration. Not every special boundary can be characterized as having the same degree of resistance to crack propagation. The interpretation of such data should also include information on the other degrees of freedom that the boundary possesses such as the grain boundary habit plane.

Previous grain boundary engineering has been sometimes successful at improving certain material properties because the introduction of new special boundaries into the microstructure may be effective in disrupting the connectivity of random boundaries. The reduction in the length of interconnected random boundary network interrupts the available pathways for the failure process. The RB network is interrupted at junctions where the RB boundary meets boundaries that are all special. In two-dimensional space, we have triple junctions where two special and one random boundaries meet (2-CSL triple junction). Thus it is possible to increase the special fraction without disrupting the random boundary network, if the special boundaries are clustered in 1-CSL or 3-CSL triple junctions. Therefore, increased special fraction is a necessary but not sufficient condition for property improvement.

In the present invention, the RGBNC may be characterized by the following procedure. Misorientations are preferably measured using electron backscatter diffraction (EBSD), or by other means well known in the art. As would be clear to one skilled in the art, the size of the sampled area should provide a statistically significant number of boundaries to be used in developing the RGBNC map. Each misorientation is categorized as being special or random with full consideration of the axis of applied stress. The random boundary data is then extracted and processed into a network format. In this manner the relevant stereological parameters may be measured, including longest or mean interconnected path, longest or mean distance from beginning to end of the network, and radius of gyration of the network. One skilled in the art may then use one or more of these stereological parameters, coupled with the service or operating environment of the material, to assess IGDF resistance.

Once the misorientations have been categorized, the interconnectivity may be determined by tracking the random networks through the microstructure. This tracking may be performed manually using the misorientation plots, preferably by a computer algorithm, or by other means well known in the art. The RGBNC may be characterized as a network of interconnecting random segments. The beginning, end, and length of each segment along with its connection to other random segments are tracked. The tracking results in a number of families of random networks that have a genealogy similar to a "family tree," because of the finite size of the sample region and the fact that random networks can start or end within the scanned area. The first boundary segment in the tree branches to multiple offspring. This branching process continues until the network is broken at a point where the random boundary encounters a break condition (or break point): a junction composed of a random boundary and other boundaries, these other boundaries being characterized as being special boundaries, random boundaries that are unfavorably oriented relative to the stress axis or combination of the foregoing. An example of unfavorably oriented random boundaries would be those wherein the direction of forward propagation of the crack lies outside of an angular range of ~120 degrees about the crack plane. In one embodiment of the present invention, the tracking is performed in two-dimensional space, wherein the break points are triple junctions comprising a random boundary, and two other boundaries (special or unfavorably oriented random). In further embodiments of the present invention, tracking of the random boundary network is not limited to two-dimensional space, and the break points are not limited solely to triple junctions, but junctions at which a random boundary meets other boundaries, all of which are special or unfavorably oriented.

FIG. 1 shows a simplified sample RGBNC map for Inconel 600 based on two dimensional tracking of identified random boundary segments in an EBSD dataset. In this figure, the special boundaries are thin black lines, and the random boundaries are heavy black lines.

The method of the present invention is applicable to polycrystalline materials, preferably to those with cubic crystalline structures. The invention may be used to assess the effectiveness of engineering processes to improve IGDF resistance. Such processes are understood to include those known as thermomechanical processes. The invention may also be used as a diagnostic tool or method to assess susceptibility of materials in service under extreme operating conditions, including high temperature, high stress, highly corrosive environments, or combinations of the foregoing.

EXAMPLES

In the following examples, samples were observed in a Hitachi S2700 SEM with an automated OIM™ attachment supplied by TSL, Inc. (Draper, Utah). Typically, the scans were carried out on a square or rectangular grid, with each orientation point being represented as a hexagonal cell, using step sizes on the order of 1–5 µm over areas approximately $4\times10^3$–$5\times10^6$ µm² in dimensions. The data include the location of each orientation (corrected for the 70 degree tilt of the sample) in Cartesian coordinates, the Euler angles representing the orientation; a measure of the image quality of the backscattered diffraction pattern, and a measure of the confidence in indexing of the EBSD patterns (confidence index) [Orientation Imaging Microscopy Software Version 2.5 User Manual. TSL, Inc., Draper, Utah, 1997]. Plots were produced of confidence index as a function of position and overlaid with boundaries in the range of 2–15 degrees (low angle) and 15–180 degrees (high angle). The Brandon criterion [Brandon, D. G., Acta metall., 1966, 14, 1479] was applied to identify those boundaries, which were special in nature, using tables produced by Adams et al. [Adams, B. L., Zhao, J. and Grimmer, H., Acta crystallogr. A, 1990, A46, 620]. Acquiring data from two to five randomly selected areas for each heat treatment made a statistical measurement of the GBCD.

The orientation data were further analyzed using software developed in-house using the IDL 5.0 (Research Systems, Inc., Boulder, Colo.) interactive data language program. The first step in data analysis was to treat data points with a low confidence index (<0.1). (Confidence index, as mentioned above, is a measure of the certainty of the pattern indexing.) Work at TSL, Inc. has shown that the certainty in indexing of a backscattered electron diffraction pattern is nearly constant for confidence indices greater than 0.1, whereas the certainty decreases sharply for lower confidence indices [Orientation Imaging Microscopy Software Version 2.5 User Manual. TSL, Inc., Draper, Utah, 1997]. An algorithm was developed to associate the orientation of a low confidence index point with that of the majority of its neighbors with common orientation. For example, it is likely that a low confidence index point will have several neighbors of common orientation. The misorientations of the six neighbors of the low confidence index point are assessed and the largest number of common-orientation contiguous neighbors is determined. The orientation of the low confidence index point and its confidence index are re-assigned from the maximum confidence index point in the list of largest number of common-orientation contiguous neighbors.

The data were then corrected for points with acceptable confidence index (>0.1) that were likely mis-indexed, such as a single point in the center of a large grain whose orientation differs from its neighbors. First, each data point was surveyed to determine the number of neighbors with differing orientation from the data point (misorientation>15 degrees). If that number was five or six, the point was considered for correction of the orientation. The neighbors were then surveyed to determine the largest number of contiguous neighbors with common orientation. If that number was five or six, then the point in question was assigned the average orientation of those five or six neighbors.

As mentioned earlier, these misorientation maps are acquired on a hexagonal grid. Thus, each orientation point can be represented as a hexagonal Voronoi cell and the neighboring hexagons meet at triple nodes. This geometry is ideal for identifying triple junctions in the microstructure, i.e. the intersection of three hexagons. As is obvious from this discussion, the geometry of quadruple or other higher order nodes cannot be considered. Plots were produced identifying the location of low-confidence-index orientation points as a function of position and overlaid with boundaries. Boundaries with $\Sigma \leq 29$ were considered to be special while boundaries with $\Sigma > 29$ were considered random. The data were then surveyed to identify the location of triple junctions in the data set. A triple junction was identified as a triple node in the hexagonal array where three boundaries intersect. The triple points were characterized and parsed among four groups: three special boundaries (S-S-S or 3-CSL), two special boundaries and one random boundary (S-S-R or 2-CSL), one special and two random boundaries (S-R-R or 1-CSL), and three random boundaries (R-R-R or 0-CSL).

Example 1

Inconel 600

An Inconel 600 alloy bar, with the measured impurity concentration as listed in Table 1, was used for the strain-crystallization (SR) processes.

TABLE 1

Elemental analysis for Inconel 600

Inconel 600

| Element | Concentration (wt %) |
|---|---|
| Ni | 74.650 |
| Cr | 16.20 |
| Mn | 0.240 |
| Si | 0.280 |
| Ti | 0.20 |
| Cu | 0.010 |
| Fe | 8.0 |
| S | 0.0020 |
| P | 0.0070 |
| Al | 0.190 |
| Co | 0.050 |
| B | 0.0010 |
| C | 0.0640 |

In the case of Inconel 600 alloy the series of optimization treatments induced a thickness reduction of 20% per rolling sequence. The bar was annealed at 1000 degrees C. for 15 minutes in air followed by water quenching. A similar sequence of straining followed by high temperature-short time annealing was performed a total of seven times. EBSD patterns observations were made after step number 1, 3, 4, 5, and 7 for a total of six observations including the as-received condition.

The break-up of the random boundary network as a function of sequential processing conditions may be seen from the RGBNC maps shown in FIGS. 2A–2C. FIG. 2(a) shows the RGBNC in the as-received material. It was quite apparent that the connectivity of the random boundaries extended through the imaging area. Extensive RB connectivity is still evident after three strain and recrystallization (SR) cycles, as shown in FIG. 2(b), even though the GBCD has improved. FIG. 2(c) shows the tremendous improvement in the break-up of the random boundary network after four SR cycles. Noteworthy is that the break-up in the connectivity of the random boundaries continues even though the GBCD increases only marginally during the later stages of the processing (4, 5, and 7 SR cycles).

Example 2

Oxygen-free Electronic (ofe) Copper

A Hitachi C10100 (99.99%) Cu bar, with the measured impurity concentration as listed in Table 2, was used for the strain-recrystallization (SR) processes.

TABLE 2

Elemental analysis for ofe-Cu
Oxygen-free electronic (ofe) copper

| Element | Concentration (p.p.m.) |
|---|---|
| H | 0.90 |
| C | 5.0 |
| O | 6.0 |
| Si | 0.20 |
| P | 0.4 |
| S | 4.0 |
| Fe | 2.0 |
| Ni | 1.0 |
| As | 0.40 |
| Se | 0.30 |
| Ag | 6.40 |
| Sb | 0.30 |
| Pb | 0.20 |

The ofe Cu was subjected to three cycles of strain-recrystallization (SR): compression to 20% strain followed by annealing. Annealing was for ten minutes at temperatures of 560 or 800 degrees C., in a box-type furnace in air.

FIGS. 3A, 3B show RGBNC maps for annealing temperatures of 560 degrees C. (FIG. 3A), and 800 degrees C. (FIG. 3B). Comparing FIGS. 3A and 3B, one can see the beneficial effects of the sequential process that were exhibited at 560 degrees C. were negated as the annealing temperature was raised to 800 degrees C. (about 0.8 $T_m$, where $T_m$ is the absolute melting temperature). This was attributed to the increased tendency for grain growth after recrystallization at the higher temperatures.

Obviously numerous modifications and variations of the present invention are possible in the light of the above teachings. It is therefore to be understood that within the scope of the appended claims the invention may be practiced otherwise than as specifically described therein.

What is claimed is:

1. A method of assessing the resistance of a test polycrystalline material to intergranular failure, the method comprising the steps of:

determining the test random grain boundary network connectivity (RGBNC) for said test material;

determining the reference RGBNC for a reference material;

wherein said RGBNC determining steps comprise:
measuring grain boundary misorientations;
categorizing said misorientation as either special or random;
tracking the beginning, end and length of each random boundary (RB) segment along with its connection to adjacent RB segments resulting in a branched network of RB segments;
continuing said tracking step until the network is broken at a point where the RB segment encounters a break point, said break point being a junction comprising a random boundary and at least two other boundaries, wherein said other boundaries are special boundaries, unfavorably oriented random boundaries, or combination of the foregoing;

determining test stereological parameters from said test RGBNC;

determining reference stereological parameters from said reference RGBNC;

wherein said stereologiral parameters are selected from the group consisting of longest interconnected path, mean interconnected path, longest distance from beginning to end of the network, mean distance from beginning to end of network, and radius of gyration of the network; and comparing said test stereological parameters to said reference stereological parameters.

2. The method as recited in claim 1 wherein:
wherein said misorientations measuring step utilizes electron backscatter diffraction.

3. The method as recited in claim 1 wherein:
said test material has been exposed to at least one extreme operating condition, said condition selected from the group consisting of high temperature, high stress, corrosive environment and combinations of the foregoing.

4. The method as recited in claim 1 wherein:
said test and reference materials are cubic crystalline materials, and said special boundaries have $\Sigma$ value $\leq 29$, and said random boundaries have $\Sigma$ value $>29$.

* * * * *